(12) United States Patent
Tahara et al.

(10) Patent No.: US 9,909,190 B2
(45) Date of Patent: Mar. 6, 2018

(54) METHOD FOR ASSISTING DETECTION OF PANCREATIC CANCER

(71) Applicant: HIROSHIMA UNIVERSITY, Higashihiroshima-shi, Hiroshima (JP)

(72) Inventors: Hidetoshi Tahara, Hiroshima (JP); Kozue Ikeda, Hiroshima (JP)

(73) Assignee: HIROSHIMA UNIVERSITY, Higashihiroshima-shi, Hiroshima (JP)

( * ) Notice: Subject to any disclaimer, the term of this patent is extended or adjusted under 35 U.S.C. 154(b) by 0 days.

(21) Appl. No.: 15/123,594

(22) PCT Filed: Mar. 3, 2015

(86) PCT No.: PCT/JP2015/056219
§ 371 (c)(1),
(2) Date: Sep. 2, 2016

(87) PCT Pub. No.: WO2015/133477
PCT Pub. Date: Sep. 11, 2015

(65) Prior Publication Data
US 2017/0073764 A1 Mar. 16, 2017

(30) Foreign Application Priority Data
Mar. 4, 2014 (JP) .................................. 2014-041594

(51) Int. Cl.
*C12Q 1/68* (2018.01)
(52) U.S. Cl.
CPC ..... *C12Q 1/6886* (2013.01); *C12Q 2600/158* (2013.01); *C12Q 2600/16* (2013.01); *C12Q 2600/178* (2013.01)
(58) Field of Classification Search
CPC ......................... C12N 15/113; C12N 2310/11
See application file for complete search history.

(56) References Cited

U.S. PATENT DOCUMENTS

2015/0184248 A1    7/2015   Tsuchiya et al.

FOREIGN PATENT DOCUMENTS

| EP | 2 518 158 A1 | 10/2012 |
| WO | WO 2007/081680 A2 | 7/2007 |
| WO | WO 2008/136971 A1 | 7/2007 |
| WO | WO 2007/103808 A2 | 9/2007 |
| WO | WO 2013/107459 A2 | 7/2013 |

OTHER PUBLICATIONS

Fulci et al. (Blood, 2007, vol. 109, No. 11, pp. 4944-4951).*
Ramon et al. (Human Reproduction, vol. 27, No. 10, pp. 3036-3045, 2012).*
Ganepola et al., "Novel blood-based microRNA biomarker panel for early diagnosis of pancreatic cancer," World J Gastrointest Oncol., Jan. 15, 2014, vol. 6, Issue 1, pp. 22-33.
Ikeda et al., "The use of plasma miRNAs in the screening of pancreatic cancer-specific biomarkers and the potential of sequence analysis with a next-generation sequencer," The 36th Annual Meeting of the Molecular Biology Society of Japan, Yoshishu, 3P-E-d, 3P-0881, Nov. 20, 2013, 2 pages.
International Search Report and English translation thereof (Form PCT/ISA/210), dated Apr. 7, 2015, for International Application No. PCT/JP2015/056219.
Janakiram et al., "Abstract 821: miRNA profiling and target identification during normal pancreata transformation to PanINs to pancreatic ductal cancer progression in p48c$^{Cre/+}$-LSL-Kras$^{G12D/+}$ mice: implication for human pancreatic cancer chemoprevention and treatment," Cancer Res, Apr. 15, 2011, vol. 71, Suppl. 8, 2 pages.
Liu et al., "Serum MicroRNA Expression Profile as a Biomarker in the Diagnosis and Prognosis of Pancreatic Cancer," Clinical Chemistry, Feb. 2012, vol. 58, No. 3, pp. 610-618.
Pan et al., "Correlation of serum microRNA profiling with pancreatic cancer risk," Acta Univ Med Nanjing, Natural Science, Nov. 2012, vol. 32, No. 11 , pp, 1541-1544, with an English abstract.
Extended European Search Report issued in European Patent Application No. 15758361.8 dated Sep. 21, 2017.
Schultz et al., "MicroRNA Expression Profiles Associated with Pancreatic Adenocarcinoma and Ampullary Adenocarcinoma", Modern Pathology, vol. 25, No. 12 (2012) pp. 1609-1622.

* cited by examiner

*Primary Examiner* — Amy H Bowman
(74) *Attorney, Agent, or Firm* — Birch, Stewart, Kolasch & Birch, LLP

(57) ABSTRACT

Disclosed is the provision of a method for assisting the detection of pancreatic cancer, the method assisting the detection of pancreatic cancer with high accuracy. In the method for assisting the detection of pancreatic cancer, the amounts of (1) miR-122-5p and (2) at least one miRNA selected from the group consisting of miR-16-5p, miR-19b-3p and miR-25-3p, all of which are contained in a test sample separated from a living body, are used as indicators. A larger amount of miR-122-5p and a smaller amount of at least one miRNA selected from the group consisting of miR-16-5p, miR-19b-3p and miR-25-3p than those in a healthy individual indicates that the living body is more likely to have developed pancreatic cancer.

5 Claims, 11 Drawing Sheets
(10 of 11 Drawing Sheet(s) Filed in Color)

miRCURY LNA™ Universal RT microRNA PCR
cDNA was synthesized by reverse transcription of total RNA and then used as a template for qRT-PCR on Serum/Plasma focused panels.

↓

Data Quality Check
Each sample showing multiple peaks detected during the melting curve analysis or each sample with an amplification efficiency of less than 1.6 was eliminated from data set.

↓

Evaluation of the Negative Control
Samples in which the difference in Ct value from the negative value was less than 5 were excluded from the data set.

↓ normalization
Normalization of each sample data was performed by the global normalization method.

↓

Data Analysis

Fig.1

Step 1: First-strand synthesis (RT)

Mature microRNA
A) ———————————————— AAAAAAAAAAAAAAAAAAAAAAA

B) ———————————————— AAAAAAAAAAAAAAAAAAAAAAA
                  ←———— TTTTTTTTTTTTTT

3' degenerate primer                    5' universal tag

Step 2: Real-time PCR amplification miR-specific forward primer
A) ————————→ ————TTTTTTTTTTTTT————
                          miR-specific reverse primer

METHOD FOR ASSISTING DETECTION OF PANCREATIC CANCER

TECHNICAL FIELD

The present invention relates to a method for assisting the detection of pancreatic cancer.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2016-09-01 0760-0466PUS1 ST25.txt" created on Sep. 1, 2016 and is 1,313 bytes in size. The sequence listing contained in this .txt file is part of the specification and is hereby incorporated by reference herein in its entirety.

BACKGROUND ART

Among various cancers, the incidence of pancreatic cancer has been increasing year by year. The westernization of meal has been pointed out as the reason for that increase. Pancreatic cancer has few initial symptoms in its early stages, enhanced proliferative capacity and highly invasive property, which currently cause an annual number of deaths almost equal to the annual number of the incidence of pancreatic cancer, and a significantly low survival rate. Pancreatic cancer is hardly detectable in some clinical examination method, such as X-ray radiography, since the pancreas is located, in the back portion of the abdomen.

Thus, methods for the detection of pancreatic cancer have been proposed, in which the amount of a microRNA (hereinafter referred to as "miRNA") in plasma is used as an indicator (Patent Documents 1 to 4).

PRIOR ART DOCUMENTS

Patent Documents

[Patent Document 1]: WO 2014/003053 A1.
[Patent Document 2]: Japanese Translated PCT Patent Application Laid-open No. 2009-521952.
[Patent Document 3]: Japanese Translated PCT Patent Application Laid-open No. 2009-528070.
[Patent Document 4]: Japanese Translated PCT Patent Application Laid-open No. 2010-577235.

SUMMARY OF THE INVENTION

Problems to be Solved by the Invention

As described above, various miRNAs have been proposed as indicators for the detection of pancreatic cancer and, needless to say, it is advantageous if pancreatic cancer can be detected with higher accuracy.

Thus, an object of the present invention is to provide a method for assisting the detection of pancreatic cancer, the method assisting the detection of pancreatic cancer with high accuracy.

Means for Solving the Problems

The inventors have found, as a result of intensive studies, that a combination of a specific miRNA whose amount is increased in pancreatic cancer and a specific miRNA whose amount is decreased in pancreatic cancer in use as indicators allows pancreatic cancer to be detected with quite high accuracy, and thereby completed the present invention.

That is, the present invention provides a method for assisting the detection of pancreatic cancer, wherein the amounts of (1) miR-122-5p and (2) at least one miRNA selected from the group consisting of miR-16-5p, miR-19b-3p and miR-25-3p, all of which are contained in a test sample separated from a living body, are used as indicators, and wherein a larger amount of miR-122-5p and a smaller amount of at least one miRNA selected from the group consisting of miR-16-5p, miR-19b-3p and miR-25-3p than those in a healthy individual indicates that the living body is more likely to have developed pancreatic cancer.

Effect of the Invention

According to the method of the present invention, pancreatic cancer can detected with high accuracy and yet simply. Thus, the method of the present invention will greatly contribute to the detection of pancreatic cancer.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 1 illustrates the flow for a comprehensive analysis of miRNAs in plasma, which was performed in Examples below.

FIG. 2 (SEQ ID NOS: 5 and 6) illustrates the principle of the measurement of miRNA amount based on reverse transcription of miRNA and on SYBR Green, which was performed in Examples below.

MODE FOR CARRYING OUT THE INVENTION

Figure 3:
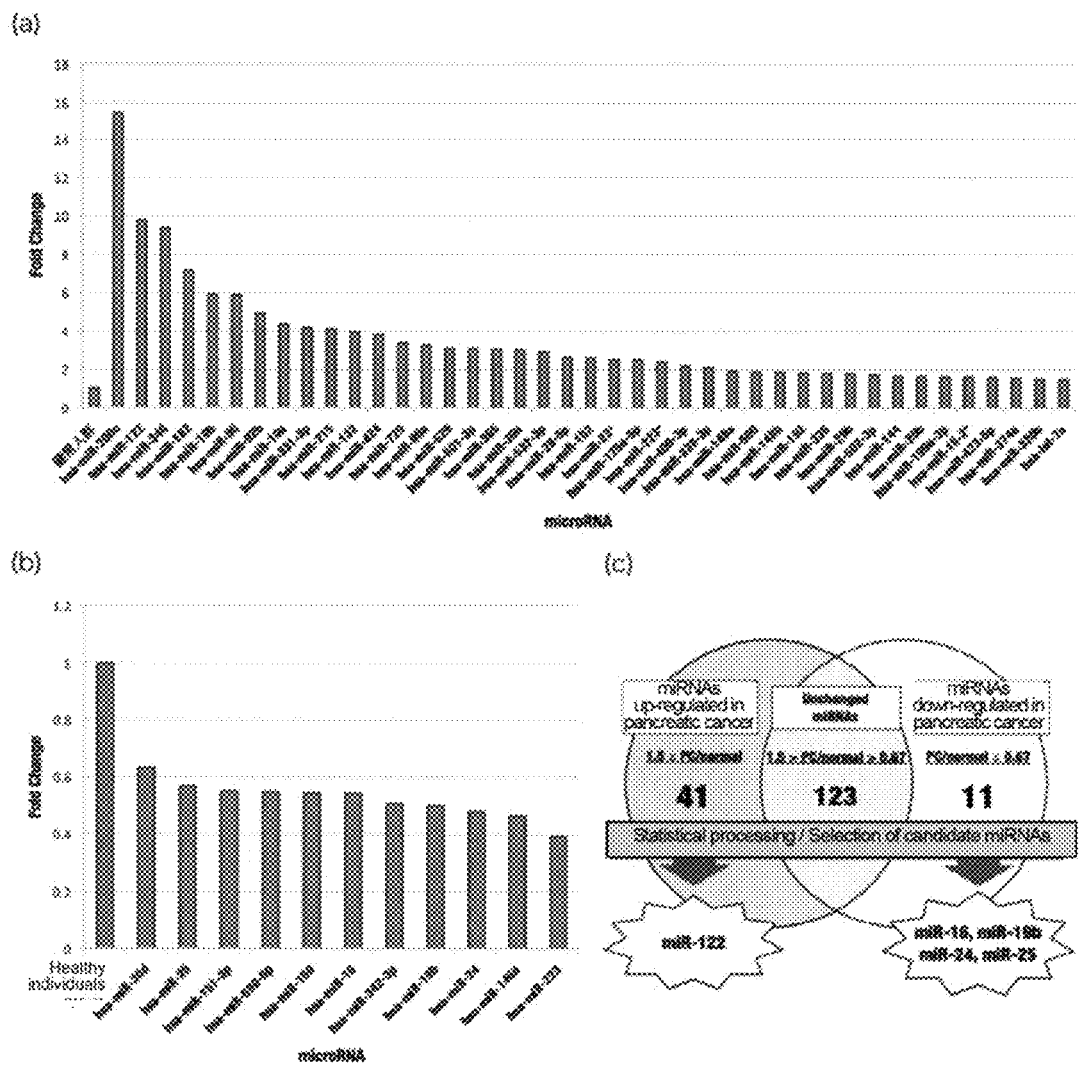
FIG. 3 shows the result of a comprehensive expression analysis of the amounts of miRNAs in plasma from the healthy individuals group and the pancreatic cancer patients group, which was performed in Examples below. (a) miRNAs whose miRNA amounts were increased 1.5-fold or more in the plasma from the pancreatic cancer patients relative to those in the plasma from healthy individuals, (b) miRNAs whose miRNA amounts were decreased 0.66-fold or less in the plasma from pancreatic cancer patients relative to those in the plasma from healthy individuals. The vertical axis represents the relative amount of a miRNA in the plasma from pancreatic cancer patients obtained by setting the amount of the same in the plasma from healthy individuals as 1. (c) The number of miRNA types whose miRNA amounts are different in the plasma from pancreatic cancer patients.

As described above, in the method of the present invention, the amounts of (1) miR-122-5p (hereinafter referred to simply as "miR-122") and (2) at least one miRNA selected from the group consisting of miR-16-5p (hereinafter referred to simply as "miR-16"), miR-19b-3p (hereinafter referred to simply as "miR-19b") and miR-25-3p (hereinafter referred to simply as "miR-25"), all of which are contained in a test sample separated from a living body, are used as indicators. These miRNAs are per se known and the base sequences thereof are indicated as follows, respectively:

miR-122:
(SEQ ID NO: 1)
uggagugugacaauggucuuug;

miR.-16:
(SEQ ID NO: 2)
uagcagcacguaaauauuggcg;

miR-19b:
(SEQ ID NO: 3)
ugugcaaauccaugcaaaacuga;

miR-25;
(SEQ ID No: 4)
cauugcacuugucucggucuga.

In these miRNAs, the amount of miR-122 is larger in pancreatic cancer patients than in healthy individuals, whereas the amounts of miR-16, miR-19b and miR-25 are smaller in pancreatic cancer patients than in healthy individuals. As specifically described in Examples below, miR-122 is a miRNA which is also significantly increased in Alzheimer's patients, and though the increase is not specific for pancreatic cancer, miR-122 allows pancreatic cancer to be detected with high accuracy in combination with the above-described specific miRNAs which are decreased in pancreatic cancer patients.

Among (2) miR-16, miR-19b and miR-25, whose amounts are decreased in pancreatic cancer patients, at least one of these is used as an indicator together with miR-122, any one of these may be used as an indicator, and miR-25 is particularly preferable. As specifically described in Examples below, the combination of miR-122 and miR-25 achieves a very high accuracy as indicated by an AUC (Area Under Curve) of 0.97 in the ROC (Receiver Operating Characteristic) curve. Since the AUC for a clinical marker in practical use is usually around 0.9, 0.97 is a very high value.

The test sample is not particularly limited as long as it is a body fluid containing miRNAs, but typically a blood sample (including plasma, serum and whole blood) is preferably used.

The quantification method for miRNA is per se well-known and all the reagents and apparatus necessary for the quantification are commercially available, so that the quantification can be readily performed by those skilled in the art. One example is specifically described in Examples below. In the method described in Examples below, a poly-A tail region is added to each miRNA at its 3' end by using commercially available reagents, and the quantification of each miRNA is performed by quantitative real-time PCR (qRT-PCR) using an oligonucleotide as a reverse primer that hybridizes to the added region and an oligonucleotide as a forward primer that hybridizes to each miRNA (both primers are commercially available). This method allows each miRNA to be quantified easily. However, the quantification method is not limited to this method, and each miRNA can be quantified, for example, by a method using a commercially available so-called "next-generation sequencer", and the like.

In the method of the present invention, if the amount of miR-122 is larger than that in a healthy individual and the amount of at least one miRNA selected from the group consisting of miR-16, miR-19b and miR-25 is smaller than that in a healthy individual, it is judged as an increased possibility of pancreatic cancer. Because a statistically significant difference (in Examples, p<0.05 in t-test) between pancreatic cancer patients and healthy individuals is observed in each miRNA used here even when it is used alone, the presence or absence of a statistically significant difference from a healthy individual is preferably used as a criterion. Specifically, preferably if the ΔCt value (cut-off value) at a plot point corresponding to the best value (the lowest value) for the false positive rate is, for example, not more than 1.31 in the combination of miR-122 and miR-25, it is judged as an increased possibility of pancreatic cancer.

Next, the present invention will be specifically described by way of examples. Of course, the present invention shall not be limited by the examples below.

EXAMPLES

Materials and Methods

Section 1. Clinical Samples

Subsection 1. Used Clinical Samples

Peripheral blood was collected based on the plan for a human genome and gene analysis research approved by the Ethics Committee of Hiroshima University for Human Genome and Gene Analysis Research. The details of the peripheral blood used for the analysis in this Example will be shown in the table below.

TABLE 1

| Sample | Abbreviation | Sample number (persons) |
| --- | --- | --- |
| Healthy individuals | normal | 58 |
| Pancreatic cancer patients (pre-operation) | PC day 0 | 50 |
| Pancreatic cancer patients (3 days post-operation) | PC day 3 | 50 |
| Alzheimer's syndrome patients | AD | 10 |
| Gastric cancer patients | GC | 6 |

Subsection 2. Recovery of Plasma from Whole Blood and Preservation of the Plasma 1) Five mL of whole blood collected in a VENOJECT II vacuum blood collection tube supplemented with EDTA-2K was transferred to a 15-mL tube and centrifuged at 3500 rpm for 10 minutes at room temperature.
2) The centrifugation produces three layers separated in the following order from the top: plasma layer, white blood cell layer, and red blood cell layer. Among those layers, only the plasma layer was transferred to a new 2-mL tube.
3) The collected plasma in the step 2 was centrifuged at 10000 rpm for 10 minutes at room temperature to precipitate blood cell components contaminated therein.
4) Only the plasma layer was aliquoted (250 µL each) into new 1.5-mL tubes and frozen at −80° C. for preservation.

Section 2. Extraction of RNA in Plasma

Extraction of RNA in plasma was performed using the miRNeasy Mini kit (QIAGEN).

1) The frozen plasma sample was thawed and centrifuged at 10000 rpm for 5 minutes at room temperature to precipitate aggregated proteins and blood cell components.
2) To a new 1.5-mL tube 200 µL of the supernatant was transferred.
3) To the tube, 1000 µL of the QIAzol Lysis Reagent was added and mixed thoroughly to denature protein components.
4) To the tube, 10 µL of 0.05 nM cel-miR-39 was added as a control RNA for RNA extraction, and the resultant was mixed by pipetting and then left to stand at room temperature for 5 minutes.
5) To promote the separation of aqueous and organic solvent layers, 200 µL of chloroform was added to the tube, and the resultant was mixed thoroughly and left to stand at room temperature for 3 minutes.
6) The tube was centrifuged at 12000× g for 15 minutes at 4° C. and the upper aqueous layer was transferred to a new 2-mL tube.
7) For the separation of RNA, 1155 µL of 100% ethanol was added to the tube, and the resulting mixture was mixed by pipetting.
8) To a miRNeasy Mini spin column (hereinafter referred to as column), 650 µL of the mixture obtained in the step 7 was transferred, and the column was left to stand at room temperature for 1 minute and then centrifuged at 8000× g for 15 seconds at room temperature to allow RNA to be adsorbed on the filter of the column. The flow-through solution from the column was discarded.
9) The step 8 was repeated until the total volume of the solution of the step 7 was filtered through the column to allow all the RNA to be adsorbed on the filter.
10) To remove impurities attached on the filter, 650 µL of Buffer RWT was added to the column, and the column was centrifuged at 8000× g for 15 seconds at room temperature. The flow-through solution from the column was discarded.
11) To clean the RNA adsorbed on the filter, 500 µL of Buffer RPE was added to the column, and the column was centrifuged at 8000× g for 15 seconds at room temperature. The flow-through solution from the column was discarded.
12) To clean the RNA adsorbed on the filter, 500 µL of Buffer RPE was added to the column, and the column was centrifuged at 8000× g for 2 minutes at room temperature. The flow-through solution from the column was discarded.
13) To completely remove any solution attached on the filter, the column was placed in a new 2-mL collection tube and centrifuged at 10000× g for 1 minute at room temperature.
14) The column was placed in a 1.5-mL tube and 50 µL of RNase-free water was added thereto, and the resultant was left to stand at room temperature for 1 minute.
15) Centrifugation was performed at 8000× g for 1 minute at room temperature to elute the RNA adsorbed on the filter. The eluted RNA was used in the following experiment without further purification and the remaining portion of the eluted RNA was stored at −80° C.

Section 3. Comprehensive Analysis of MicroRNA in Plasma

Subsection 1. Principle of the Comprehensive Analysis

Comprehensive analysis of miRNAs in plasma was performed using the miRCURY LNA™ Universal RT microRNA, PCR, Polyadenylation and cDNA synthesis kit, the microRNA Ready-to-Use PCR, Human panel I and panel II (Exiqon). The flow for the analysis is shown in FIG. 1. Moreover, the measurement principle is shown in FIG. 2.

The polyadenylation and cDNA synthesis kit is a cDNA synthesis kit for miRNA designed to allow all miRNAs in a sample to be reverse-transcribed in one tube through the addition of a poly-A tail to the 3' end of a mature miRNA and the reverse transcription using a primer including a poly-T primer (FIG. 2, Step 1).

The microRNA Ready-to-Use PCR, Human panel I and panel II is a set of 384-well plates deposited with freeze dried primers that allows 175 miRNA types to be measured. A PCR reaction starts and proceeds by addition of the synthesized cDNA and the SYBR Green master mix, a reaction reagent in which an enzyme and a fluorescent material are mixed, to this set, and allows the amount of a miRNA in the sample to be determined as the difference between fluorescence intensities (FIG. 2. Step 2). The second derivative method was used in the calculation of a Ct value, with which the Ct value is determined to correspond to a point showing the maximum change of fluorescence in the amplification curve, while the ΔΔCt method was used for the analysis, in which the amounts of miRNAs are relatively compared without generating a standard curve. This is also applicable to the subsequent qRT-PCR analysis.

Subsection 2. Normalization of Ct Value in the Comprehensive Analysis

In this Example, the concentration of the RNA solution was not adjusted because the amount of RNA extractable from the plasma was very small and therefore the determination of the concentration was difficult. Accordingly, the analysis compared samples not with regard to "how much amount of a miRNA of interest had been contained in the same mass of RNA" but with regard to "how much amount of a miRNA of interest had been contained in the solution of RNA extracted from the same volume of plasma". This is also applicable to the subsequent qRT-PCR analysis.

The results determined in a contracted analysis were normalized among samples by the global normalization method and the normalized results were analyzed.

The global normalization method is a method in which the mean Ct values of all miRNA types are matched with each other based on the assumption that almost the same total amount of miRNAs is contained in each sample and the amounts of the vast majority of miRNAs are invariable. Specifically, the normalization was performed among samples using the mean Ct value as described below.

1) Out of 175 miRNA types measured, miRNAs detected in all the samples were selected.
2) The mean Ct value of all the selected miRNAs was calculated.
3) The calculated mean Ct value was used as a correction value, which was subtracted from the Ct value of each mRNA to produce the corrected Ct value (ΔCt value) for use of analysis.

Section 4. Quantification of MicroRNA in Plasma by qRT-PCR

Subsection 1. Reverse Transcription of MicroRNA

Reverse transcription of miRNAs in plasma was performed using the Universal cDNA Synthesis Kit (EXIQON).
1) The RT master mix was prepared in a 0.65-mL tube as shown below.

TABLE 2

| reagent | volume (μL)/sample |
| --- | --- |
| 5x reaction buffer | 2 |
| Nuclease-free water | 5 |
| Enzyme mix | 1 |
| total | 8 |

2) The mixture was mixed by tapping the tube and then spun down and aliquoted at 8 μL per each tube of an 8-tube strip.
3) To the tube 2 μL of RNA extracted from the plasma as added and mixed thoroughly by pipetting.
4) A reverse transcription reaction was performed using the GeneAmp (trade name) PCR System 9700 (Applied Biosystems) under the following conditions.

TABLE 3

|  | Step 1 | Step 2 | Step 3 |
| --- | --- | --- | --- |
| temperature (° C.) | 42 | 95 | 4 |
| time (min.) | 60 | 5 | ∞ |

5) The synthesized cDNA was transferred to a new 0.65-mL tube and stored at −80° C.

Subsection 2. qRT-PCR with SYBR Green

A real-time PCR reaction was performed using the LightCycler (trade name) 480 SYBR Green I Master (Roche), the KAPA SYBR (trade name) FAST Master Mix (2x) Universal (Nippon Genetics), and the LightCycler (trade name) 480 Multiwell Plate 384, white (Roche) as a 384-well plate. A PCR reaction mix and diluted cDNA were dispensed to the 384-well plate using the Bravo Automated Liquid Handling Platform (Agilent Technologies).

1) The synthesized cDNA was diluted 40 times in DNase-free water in a 0.65-mL tube.
2) A PCR reaction mix was prepared in a 0.65-mL tube as follows (the indicated amounts are per one sample in a single replicate).

TABLE 4

| reagent | volume (μL)/sample |
| --- | --- |
| PCR primer (10x) | 1 |
| master mix (2x) | 5 |
| total | 6 |

3) The PCR reaction mix was aliquoted at 6 μL per each well of the 384-well plate.
4) The diluted cDNA prepared in the step 1 was aliquoted at 4 μL per each well of the 384-well plate, and the resultant was mixed thoroughly by pipetting.
5) The 384-well plate was sealed to prevent evaporation of the sample and centrifuged at 1500x for 1 minute at room temperature.
6) Real-time PCR was performed using the LightCycler (trade name) 480 (Roche) under the following conditions.
*In cases where LightCycler (trade name) 480 SYBR Green I Master (Roche) is used.

TABLE 5

|  | temperature | time | temperature/second | |
| --- | --- | --- | --- | --- |
| Pre-Incubation | 95° C. | 10 min | 4.8 | |
| Amplification | 95° C. | 10 sec | 2 | 45 cycles |
|  | 60° C. | 30 sec | 2 | |
| Melting curve | 95° C. | 5 sec | 4.8 | |
|  | 65° C. | 1 min | 2.5 | |
|  | 97° C. | — | 0.11 | |
| Cooling | 40° C. | 30 sec | 2.5 | |

TABLE 6

|  | temperature | time | temperature/second | |
| --- | --- | --- | --- | --- |
| Pre-Incubation | 95° C. | 30 sec | 4.8 | |
| Amplification | 95° C. | 10 sec | 2 | 45 cycles |
|  | 60° C. | 30 sec | 2 | |
| Melting curve | 95° C. | 5 sec | 4.8 | |
|  | 65° C. | 1 min | 2.5 | |
|  | 97° C. | — | 0.11 | |
| Cooling | 40° C. | 30 sec | 2.5 | |

Subsection 3. Analysis of the Results

The second derivative method was used in the calculation of a Ct value, with which the Ct value is determined to correspond to a point showing the maximum change of fluorescence in the amplification curve, while the ΔΔCt method was used for the analysis, in which the amounts of miRNAs are relatively compared without generating a standard curve. Moreover, the amount of miRNA should be normalized to make comparison among samples and the external control cel-miR-39 added in the step 4 in the section 2 was used for the normalization. A method to calculate a normalized value (ΔCt value) is shown below:

$$\Delta Ct = Ct - Ct_{cel\text{-}miR\text{-}39}.$$

In the qRT-PCR analysis following the second screening, a ΔCt value obtained according to the above equation, that is, by subtracting the Ct value of cel-miR-39 contained in a measured sample from a Ct value in the same sample was used for analysis.

Results

Section 1. Identification of MicroRNAs in Plasma that Exhibit a Variation Specific for Pancreatic Cancer Patients Subsection 1.

In this section, the miRNA profiles in the plasma from healthy individuals and pancreatic cancer patients were comprehensively analyzed and compared to identify miRNAs that were variable in pancreatic cancer patients.

Subsection 2. Comprehensive Analysis and Comparison of MicroRNAs in the Plasma from Healthy Individuals and Pancreatic Cancer Patients (the First Screening)

The microRNA Ready-to-Use PCR, Human panel I and panel II was used to comprehensively analyze the amounts of 175 miRNA types in the plasma from four each from a group of healthy individuals in their twenties, a group of healthy individuals in their forties, a group of healthy individuals in their sixties and a group of pancreatic cancer patients, and to compare the amounts of miRNAs in each group. The mean of the amount of each miRNA was calculated in each group and it was compared among the groups. The data with regard to the clinical samples used in the analysis is as shown in Table 7.

First, a comparison was made between the group of healthy individuals in their sixties and the group of pancreatic cancer patients to explore miRNAs that were variable in plasma. Since pancreatic cancer is more likely to develop in the elderly than in the young and, moreover, the average age of the four pancreatic cancer patients used here was 60.25 years old, the group of healthy individuals in their sixties was selected as a control group. The result of the comparison between both groups is shown in FIG. 3. FIG. 3(a) shows miRNAs whose miRNA amounts in plasma have been increased 1.5-fold or more in the group of pancreatic cancer patients relative to those in the group of healthy individuals in their sixties, and (b) shows miRNAs whose miRNA amounts in plasma have been decreased 0.66-fold or less in the group of pancreatic cancer patients relative to those in the group of healthy individuals in their sixties. Out of 175 miRNA types examined in the first screening, the amounts of 41 miRNA types in plasma were increased 1.5-fold or more in the group of pancreatic cancer patients, while the amounts of 11 miRNA types in plasma were decreased 0.66-fold or less in the group of pancreatic cancer patients (total 52 types).

The t-test was performed on the amounts of these 52 miRNA types in plasma.

Five miRNA types (miR-122, miR-16, miR-19b, miR-24 and miR-25) which had a significant difference at the 5% level in the t-test and had been detected (the difference in Ct value from the negative control was not less than 5) in all of the twelve samples measured here were further analyzed as marker candidate miRNAs for pancreatic cancer.

A miRNA whose amount in plasma was increased in pancreatic cancer patients as compared to health individuals: miR-122.

miRNAs whose amounts in plasma were decreased in pancreatic cancer patients as compared to healthy individuals: miR-16, miR-19b, miR-24, miR-25.

TABLE 7

| Group | Sample No. | Gender | Age (years old) | Average age (years old) |
|---|---|---|---|---|
| Healthy individuals in their twenties | NR-512 | Female | 23 | 22 |
| | NR-626 | Female | 21 | |
| | NR-744 | Male | 21 | |
| | NR-960 | Male | 23 | |
| Healthy individuals in their forties | NR-560 | Female | 44 | 43 |
| | NR-629 | Female | 41 | |
| | NR-1034 | Male | 41 | |
| | NR-1087 | Male | 46 | |
| Healthy individuals in their sixties | NR-484 | Female | 64 | 66 |
| | NR-556 | Male | 68 | |
| | NR-1081 | Male | 64 | |
| | NR-1089 | Female | 68 | |
| Pancreatic cancer patients | 1 | Female | 60 | 60.25 |
| | 3 | Male | 62 | |
| | 4 | Male | 56 | |
| | 5 | Female | 63 | |

Subsection 3. Comparison of the Amounts of Marker Candidate MicroRNAs Between Healthy Individuals and Pancreatic Cancer Patients by qRT-PCR (Second Screening)

The differences between the healthy individuals and the pancreatic cancer patients demonstrated in the first screening with respect to the amount of miRNA in plasma may be considered to be substantially influenced by individual differences in each sample used in the experiment. Then, in order to eliminate the influence of the individual differences on the amounts of the marker candidate miRNAs in plasma, the sample number was increased to 50 in each of the group of healthy individuals not younger than 60 years of age and the group of pancreatic cancer patients and, as the second screening, the amount of the individual candidate miRNA in the plasma of each sample was measured by qRT-PCR. The gender and the average age in the clinical samples used in the measurement are as shown in Table 8. The group of pancreatic cancer patients is composed of patients all corresponding to the stages III and IVa based on the UICC classification. As described in the subsection 2, since pancreatic cancer has a tendency to develop at an advanced age, healthy individuals not younger than 60 years of age were selected for a control group. The determination of the amounts of the marker candidate miRNAs in the second screening was performed by the qRT-PCR method using SYBR Green.

TABLE 8

| Group | Sample number | Sex ratio (male/female) | Average age (years old) |
|---|---|---|---|
| Group of healthy individuals not younger than 60 years of age | 50 | 25/25 | 66.9 |
| Group of pancreatic cancer subjects | 50 | unknown | — |

Figure 4:
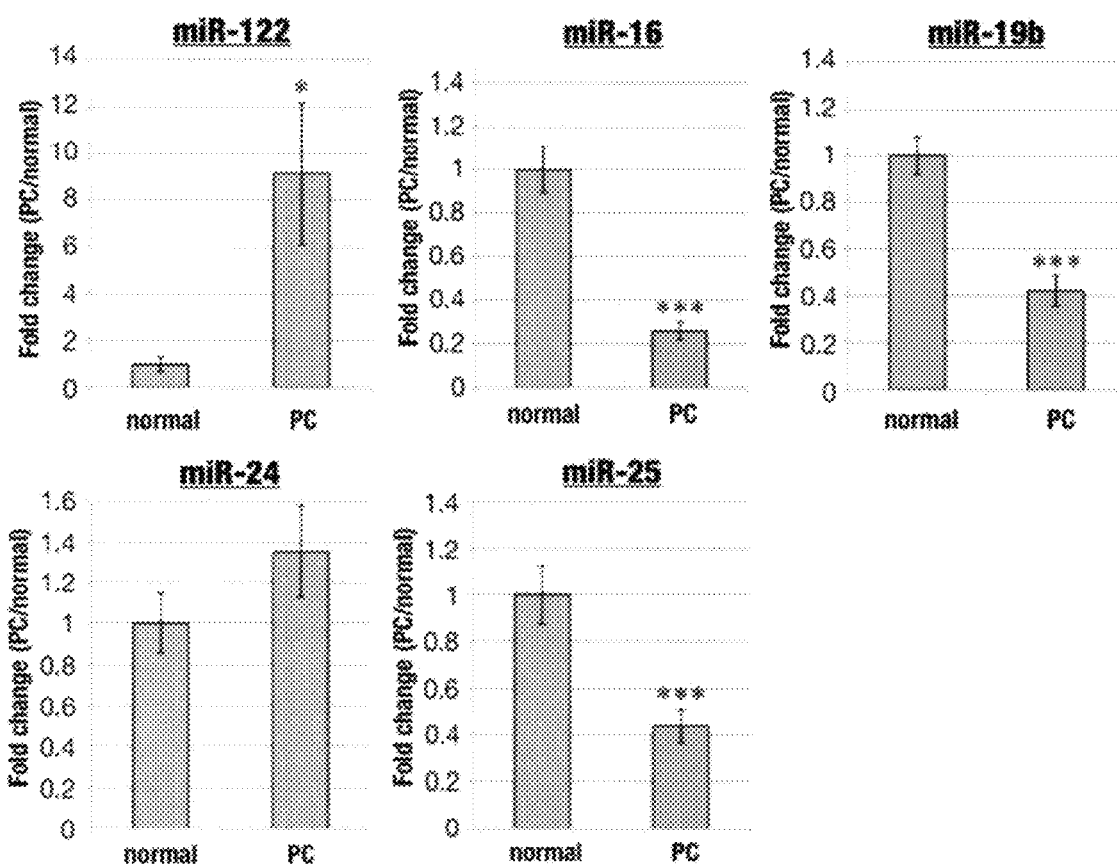
FIG. 4 is a diagram showing the comparison of the amounts of miRNAs as marker candidates between the healthy individuals group and the pancreatic cancer patients group, which was obtained in Examples below. The vertical axis represents the relative amount of a miRNA obtained by setting the mean of the amount of the same in healthy individuals as 1. normal: the healthy individuals group, PC: the pancreatic cancer patients group, *: $p<0.05$, : $p<0.005$, *: $p<00005$.
Figure 5:
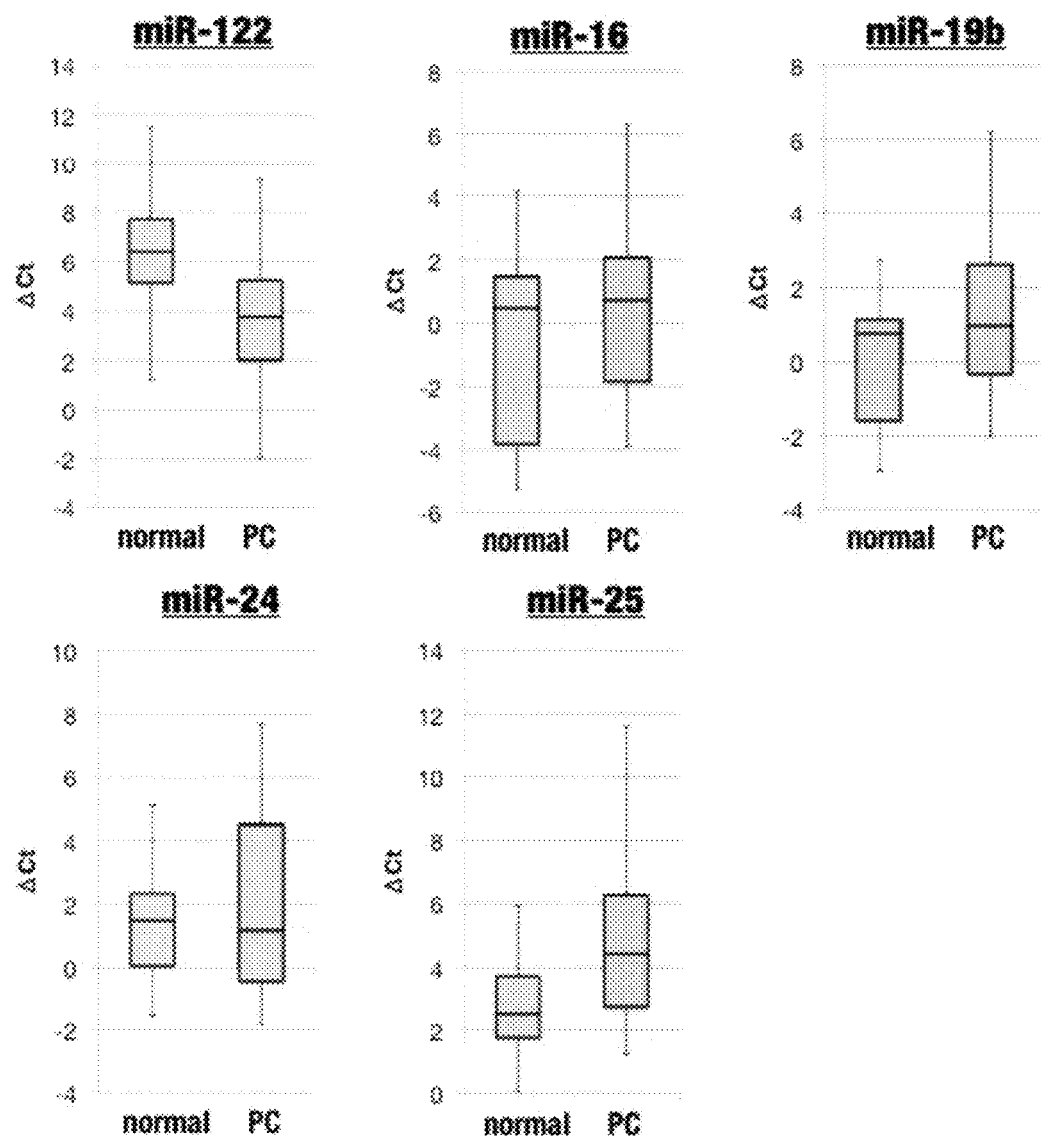
FIG. 5 is a diagram showing the distribution of the amount of each miRNA in each group, which was obtained in Examples below. The vertical axis represents a $\Delta Ct$ value obtained by normalizing a Ct value with an external control. normal: the healthy individuals group, PC: the pancreatic cancer patients group.

The result is shown in FIG. 4. Out of the five marker candidate miRNA types, it was four types including miR-122, miR-16, miR-19b and miR-25 and excluding miR-24 that exhibited a similar tendency to the result in the first screening with respect to the difference in the amount of miRNA between the healthy individuals group and the pancreatic cancer patients group. In the first screening, miR-24 tended to decrease in the pancreatic cancer patients group, while in the second screening where the sample number was increased, it rather tended to increase, indicating the opposite result. When the t-test was performed on each of the miRNAs, a significant difference at the 5% level was obtained in four miRNA types including miR-122, miR-16, miR-19b and miR-25. Then, the distribution of the amount of a miRNA in both groups is shown in FIG. 5. A ΔCt on the vertical axis represents a value obtained by normalizing a Ct value measured by qRT-PCR with an external control. As compared to the healthy individuals group, miR-122 showed an increasing tendency and miR-16, miR-19b and miR-25 showed a decreasing tendency in the pancreatic cancer patients group. In miR-24, the distribution of the amount of the miRNA was overlapped between the healthy individuals group and the pancreatic cancer patients group, indicating no difference between them.

From the above result, we decided to further analyze miR-122 as well as miR-16, miR-19b and miR-25 as marker candidate miRNAs far the diagnosis of pancreatic cancer, wherein the former one was considered to be a miRNA whose amount in plasma had an increasing tendency and the latter three were considered to be miRNAs whose amounts in plasma had an decreasing tendency in pancreatic cancer patients relative to healthy individuals.

Subsection 4. Validation of the Influence of Age and Gender on Marker Candidate MicroRNAs Four marker candidate miRNA types for pancreatic cancer have been identified by conducting the second screening in the subsection 3. However, the influence on the age and gender in the pancreatic cancer patients group has not been considered. It was conceivable that the variation of the amount of miRNA due to the disease might not be detected in cases where the identified marker candidate miRNAs would be influenced by age and/or gender. Thus, we examined based on the measurement results of the first screening how much extent the amounts of these miRNAs in plasma were influenced by age and/or gender. The clinical samples used for the examination of the influence of age are the healthy individuals in each generation described in Table 7 in the subsection 2, while those used for the examination of the influence of gender are the healthy individuals not younger than 60 years of age described in Table 8 in the subsection 3.

Figure 6:
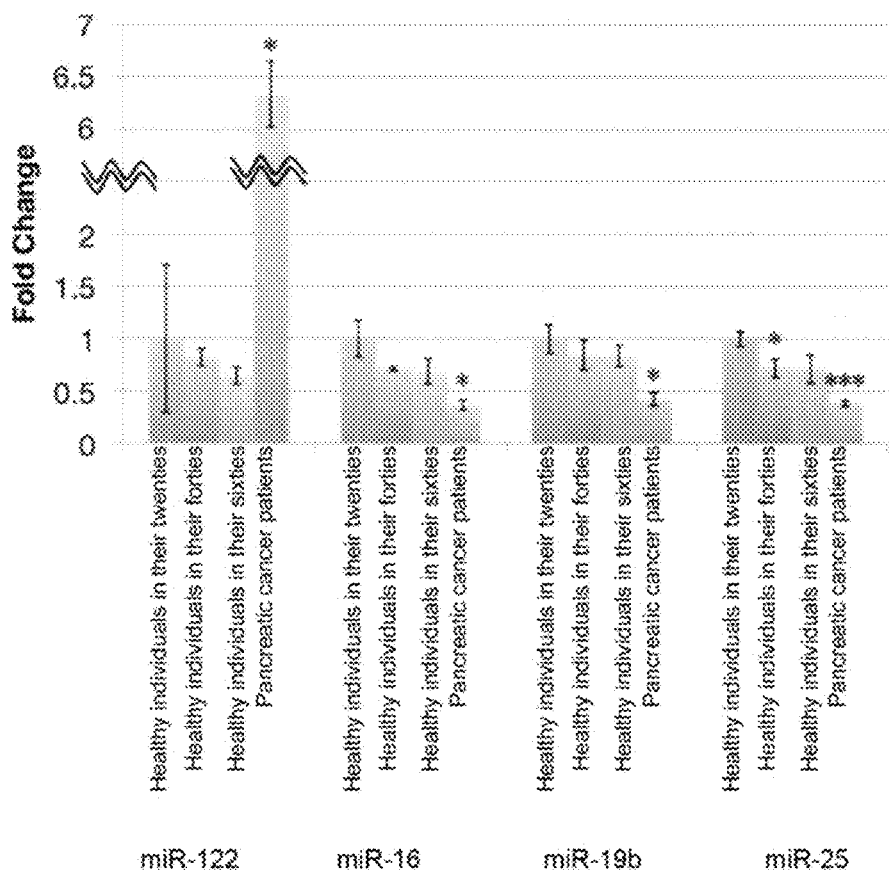
FIG. 6 is a diagram showing the influence of age on miRNAs as marker candidates, which was obtained in Examples below. The vertical axis represents the relative amount of a miRNA obtained by setting the mean of the amount of the same in healthy individuals in their twenties as 1. *: p<0.05, : p<0.005, *: p<0.0005.
Figure 7:
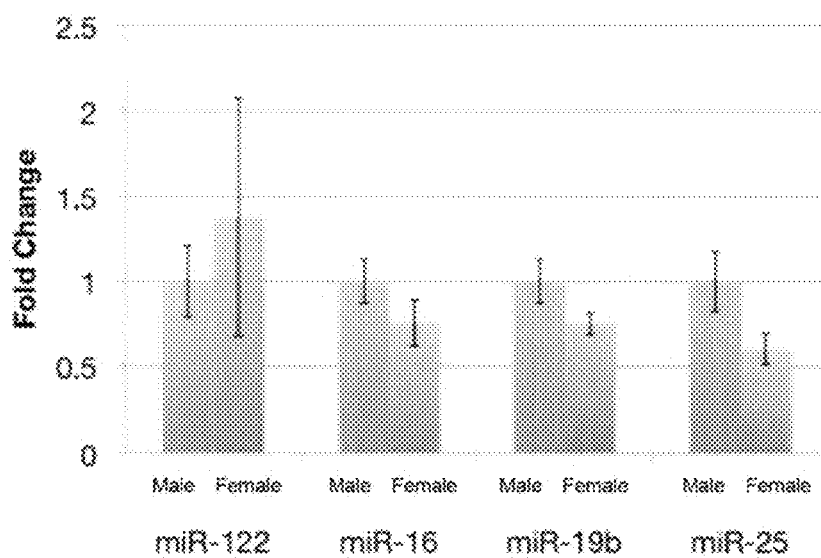
FIG. 7 is a diagram showing the influence of gender on miRNAs as marker candidates, which was obtained in Examples below. The vertical axis represents the relative amount of a miRNA obtained by setting the mean of the amount of the same in male individuals as 1.

The influence of age and the influence of gender on the marker candidate miRNAs are shown in FIG. 6 and FIG. 7, respectively. When the test was performed, a significant difference in the amount of miR-25 in plasma at the 5% level was obtained between the healthy individuals in their twenties and in their forties, suggesting the influence of age on miR-25 including a possible slight decreasing tendency due to ageing. However, as a whole, any significant difference by age and gender is undetectable with respect to the amount of each marker candidate miRNA in plasma. Although a significant difference by age was observed in the amount of miR-25 in plasma, it is apparent that the difference between healthy individuals and the pancreatic cancer patients is larger than that by age. From the above result, it has been found that age and gender do not significantly influence on the amounts of the marker candidate miRNAs for pancreatic cancer in plasma and do not interfere with the usage thereof as diagnostic markers.

Subsection 5. Summary

As miRNAs whose amounts in plasma vary according to the development of pancreatic cancer and are different between healthy individuals and pancreatic cancer patients, five types were identified as candidates in the first screening and four types including miR-122, miR-16, miR-19b and miR-25 were identified in the second screening. Because the difference in the amounts of these miRNAs is apparently statistically significant and, moreover, those amounts are hardly influenced by age and gender, those miRNAs are believed to be applicable as diagnostic markers. Particularly, considering the onset age of pancreatic cancer characterized in that the incidence of pancreatic cancer is rare in individuals at an age younger than 40 years and gradually increases with advance of age from late forties to fifties and individuals in their sixties to eighties account for 80% of the total incidence of pancreatic cancer, the four microRNA types including miR-122, miR-16, miR-19b and miR-25 are absolutely free from the influence of age and gender. In the following sections, the usefulness of the identified four miRNA types in the diagnosis of pancreatic cancer was farther examined.

Section 2. Validation of the Specificity of Marker Candidate MicroRNAs for Pancreatic Cancer Patients Subsection 1.

Four miRNA types have been identified as marker candidate miRNAs for pancreatic cancer in the section 1. However, it remains unclear whether the difference in the amount of miRNA in plasma demonstrated for these miRNAs is specific for pancreatic cancer patients or the amount of each miRNA in plasma also varies in a nonspecific manner under other diseases. Then, in this section, the amount of each marker candidate miRNA in plasma in diseases other than pancreatic cancer was measured and compared to those in healthy individuals and pancreatic cancer patients to examine the specificity of the identified miRNAs for pancreatic cancer patients.

Subsection 2. Measurement and Comparison of the Amounts of Marker Candidate MicroRNAs in Diseases other than Pancreatic Cancer The amounts of the four marker candidate miRNA types identified in the section 1 were measured in the plasma from 16 patients suffering from diseases other than pancreatic cancer and were compared to those in the plasma from 50 healthy individuals and 50 pancreatic cancer patients. The samples indicated in Table 8 in the subsection 3, the section 1 were used as those form the healthy individuals and pancreatic cancer patients. Alzheimer's syndrome and gastric cancer were selected as the diseases other than pancreatic cancer (Table 9). Alzheimer's syndrome was selected as a disease whose incidence rate is high in the elderly similarly to that of pancreatic cancer, while gastric cancer was selected as a cancer disease different from pancreatic cancer. The measurement here was performed by the qRT-PCR method using SYBR Green.

TABLE 9

| Disease | Sample number | Sex ratio (male/female) | Average age (years old) |
|---|---|---|---|
| Alzheimer's syndrome | 10 | 5/5 | 74.2 |
| Gastric cancer | 6 | 4/2 | 78.7 |

Figure 8:
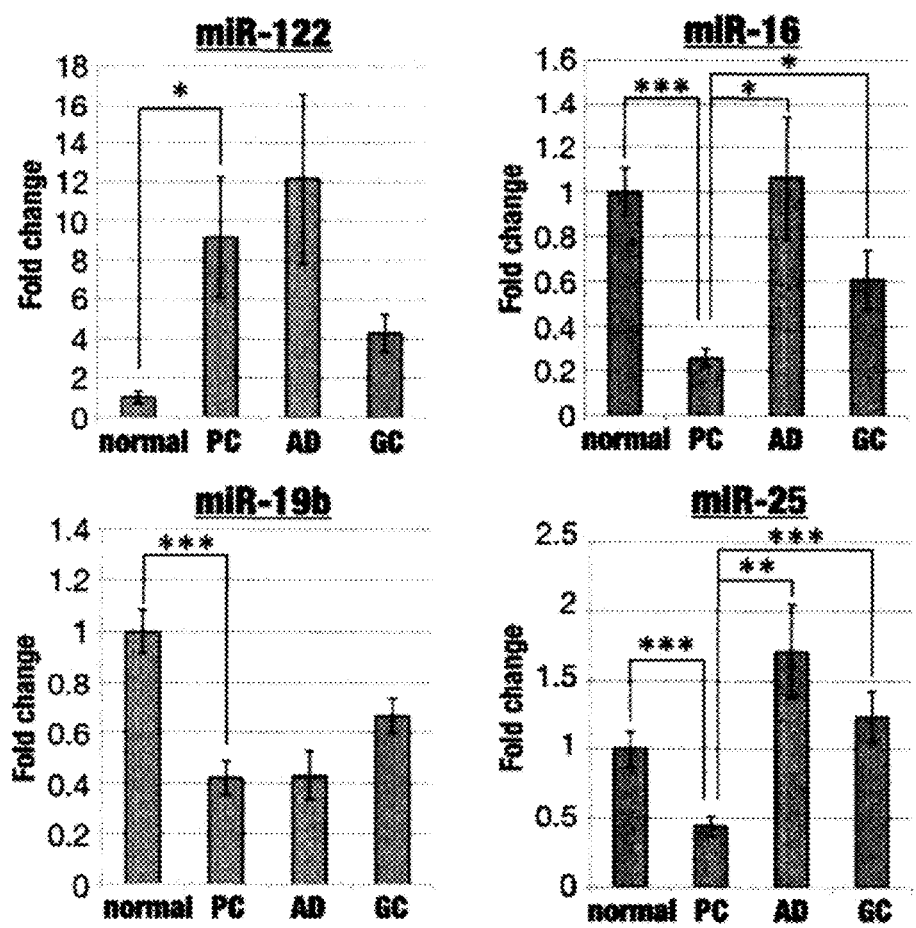
FIG. 8 is a diagram showing the comparison of the amounts of miRNAs as marker candidates in the plasma from patients with other diseases, which was obtained in Examples below. The vertical axis represents the relative amount of a miRNA obtained by setting the mean of the amount of the same in healthy individuals as 1, normal: the healthy individuals group, PC: the pancreatic cancer patients group, AD: Alzheimer's syndrome patients group. GC: gastric cancer patients group, *: p<0.05, : p<0.005, : p<0.0005.

The result is shown in FIG. 8. The amount of each marker candidate miRNA was compared among the healthy individuals group, the pancreatic cancer patients group, the Alzheimer's syndrome patients group and the gastric cancer patients group, and the t-test was performed between the pancreatic cancer patterns group and the other disease patients groups. As a result, a significant difference at the 5% level was obtained in rniR-16 and miR-25, suggesting a possible variation of the amounts of these two miRNA types in plasma in a manner specific for pancreatic cancer patients.

On the other hand, because a significant difference between the pancreatic cancer patients group and the other disease patients group was not obtained in miR-122 and miR-19b, a low specificity thereof for pancreatic cancer patients was suggested.

The miR-122 is a miRNA highly expressed in liver and is known to be abundant in the plasma of patients suffering from hepatitis or liver cancer. Thus, it may be released in blood with the dislodgement of liver cells and detected at a high level in plasma when any damage has occurred in the liver. Moreover, it may be packaged in exosomes, a type of extracellular vesicle, and secreted from liver cells themselves. All of the pancreatic cancer patients used in this study are patients at the stages III and IVa and appropriate for surgery, in which a distant metastasis to the liver has not been observed. However, since a metastasis to organs adjacent to the pancreas (such as the stomach) and or lymph nodes close to the pancreas is observable in patients at the stages III and IVa, it is conceivable that undetectable metastatic foci may have been formed in the liver.

With regard to miR-19b, similarly to the amount of the miRNA in the pancreatic cancer patients, it was decreased in the Alzheimer's syndrome patients and the gastric cancer patients as compared to the healthy individuals, suggesting the relationships of the miRNA with various diseases.

Figure 9:
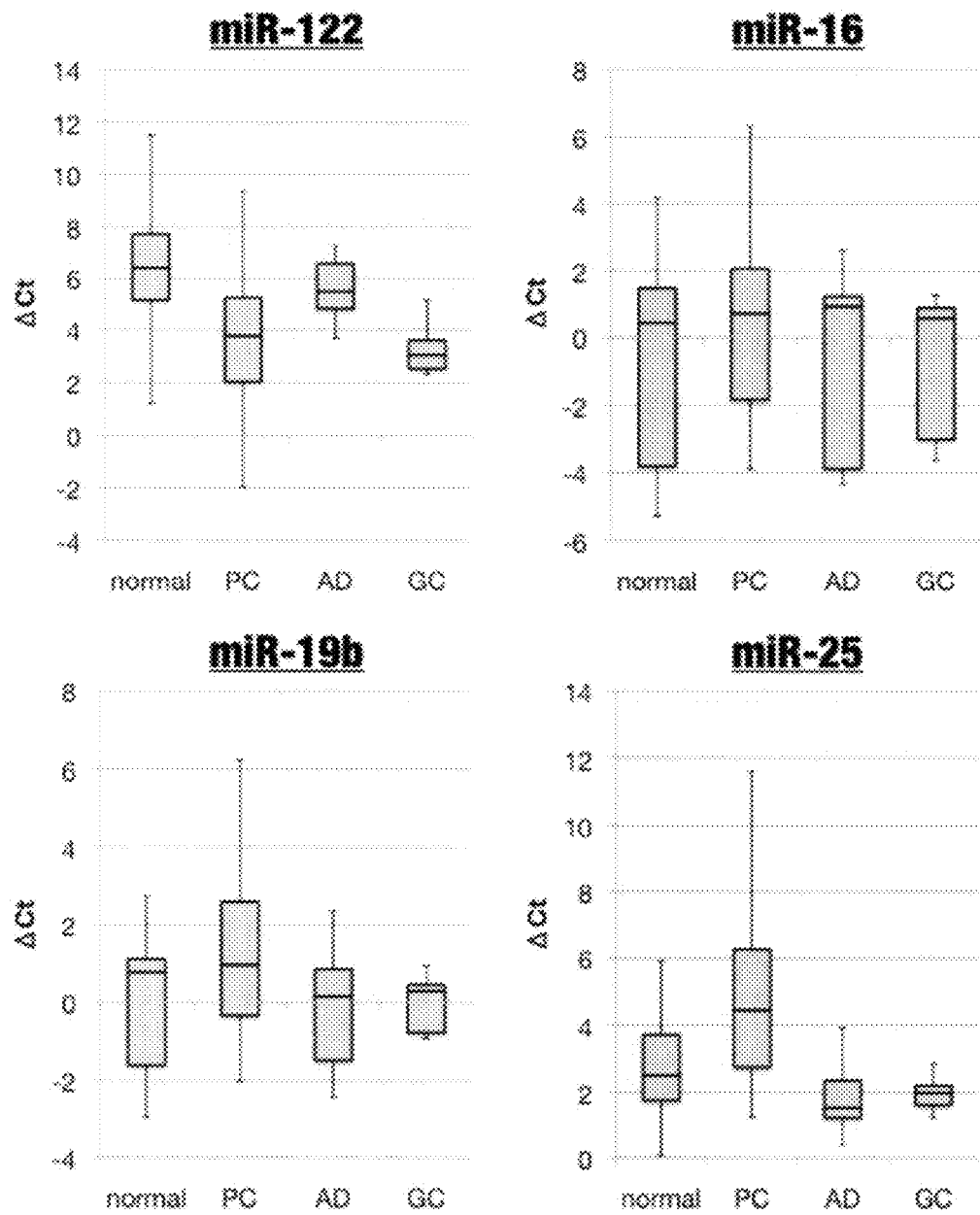
FIG. 9 is a diagram showing the distribution of the amount of each miRNA as a marker candidate in the plasma from each sample, which was obtained in Examples below. The vertical axis represents a ΔCt value obtained by normalizing a Ct value with an external control. normal: the healthy individuals group, PC: the pancreatic cancer patients group, AD: Alzheimer's syndrome patients group, GC: gastric cancer patients group.

The distribution of the amount of each marker candidate miRNA in each group is shown in FIG. 9. When the collective tendency of the amount of each marker miRNA in plasma is examined, the range of values between the 25% and the 75% is shown to be broad in miR-16, indicating a larger individual difference among samples as compared to those in the other marker miRNAs. It is understand that a significant difference at the 0.5% level was obtained in miR-25, as demonstrated in FIG. 8, since the difference between the pancreatic cancer patients group and the other groups was clear.

Subsection 3. Summary

By the comparison with patients suffering from diseases other than pancreatic cancer, in which Alzheimer's syndrome patients and gastric cancer patients were used, miR-16 and miR-25 were suggested to potentially vary the amounts in plasma in a manner specific for pancreatic cancer patients. Because miR-122 and miR-19b exhibited similar tendencies in the Alzheimer's syndrome patients and the gastric cancer patients to those in the pancreatic cancer patients with respect to the variation of the amount of miRNA in plasma, it has been indicated that the variation of these miRNAs is not specific for pancreatic cancer patients.

From the above result, it has been indicated that miR-16 and miR-25 out of the examined four miRNAs are useful as diagnostic markers for pancreatic cancer. Moreover, although any specificity for pancreatic cancer patients was not observed in miR-122 and miR-19b, the combination with miR-16 and/or miR-25 may allow them to be used as markers playing such an auxiliary role as to increase the accuracy of the diagnosis.

Section 3. Validation of the Diagnostic Accuracy of Marker MicroRNAs Using $\Delta$Ct Values Subsection 1.

The previous experimental results have indicated that the amounts of the four marker miRNA types in plasma were different between healthy individuals and pancreatic cancer patients. However, in cases where these marker miRNAs are used for the diagnosis of pancreatic cancer, the accuracy to differentiate between positivity and negativity for pancreatic cancer is critical. Moreover, because a screening test in hospital laboratories to measure the test values is contemplated, a convenient measurement method is preferable. From the above viewpoints, the usefulness thereof as diagnostic markers was examined in this study by focusing on a $\Delta$Ct value, which can be easily calculated from results of a qRT-PCR measurement.

Subsection 2. Evaluation of the Accuracy of Marker MicroRNAs with ROC Curve

A method of plotting a ROC (Receiver Operating Characteristic) curve and calculating an AUC for comparison is a method to evaluate the accuracy of a diagnostic marker. ROC represents a curve obtained by plotting "1—Specificity" (false positive rate) on the horizontal axis and "Sensitivity" on the vertical axis with varying cut-off values as a parameter that determines positive and negative outcomes. AUC (Area Under Curve) refers to the area under the ROC curve and an AUC value ranges from 0.5 to 1. When a ROC curve is plotted and an AUC is calculated by using a certain diagnostic marker, an AUC Value closer to 1 means that the diagnostic marker is evaluated as a more precise marker. In this study, the accuracy of the four marker miRNA types was evaluated using this method. The $\Delta$Ct values from the samples shown in Tables 8 and 9 were used to create ROC curves. The healthy individuals, the Alzheimer's syndrome patients, and the gastric cancer patients were selected as non-pancreatic cancer patient samples.

Figure 10:
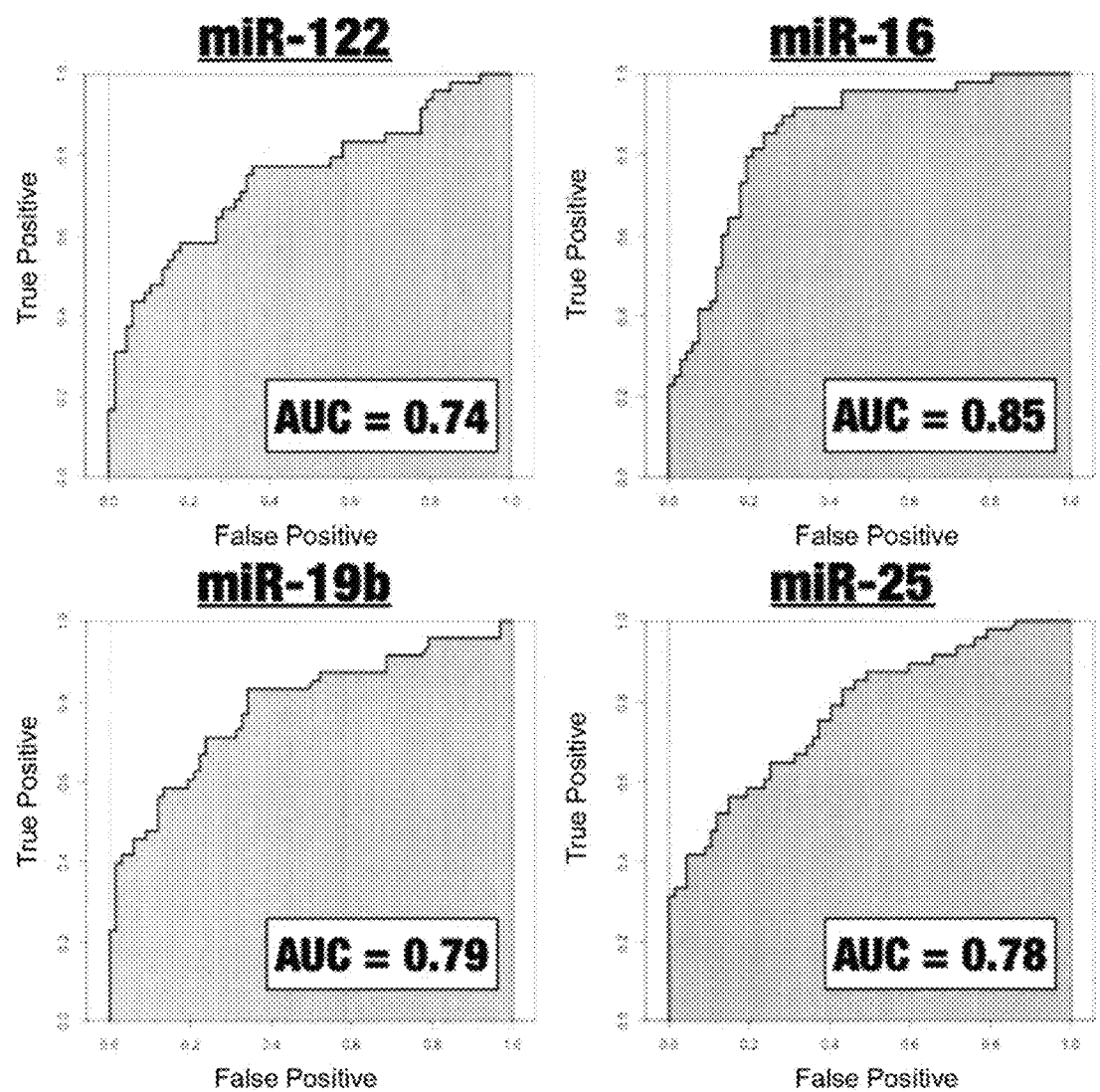
FIG. 10 shows ROC curves based on the ΔCt value of each marker miRNA, which were obtained in Examples below.
Figure 11:
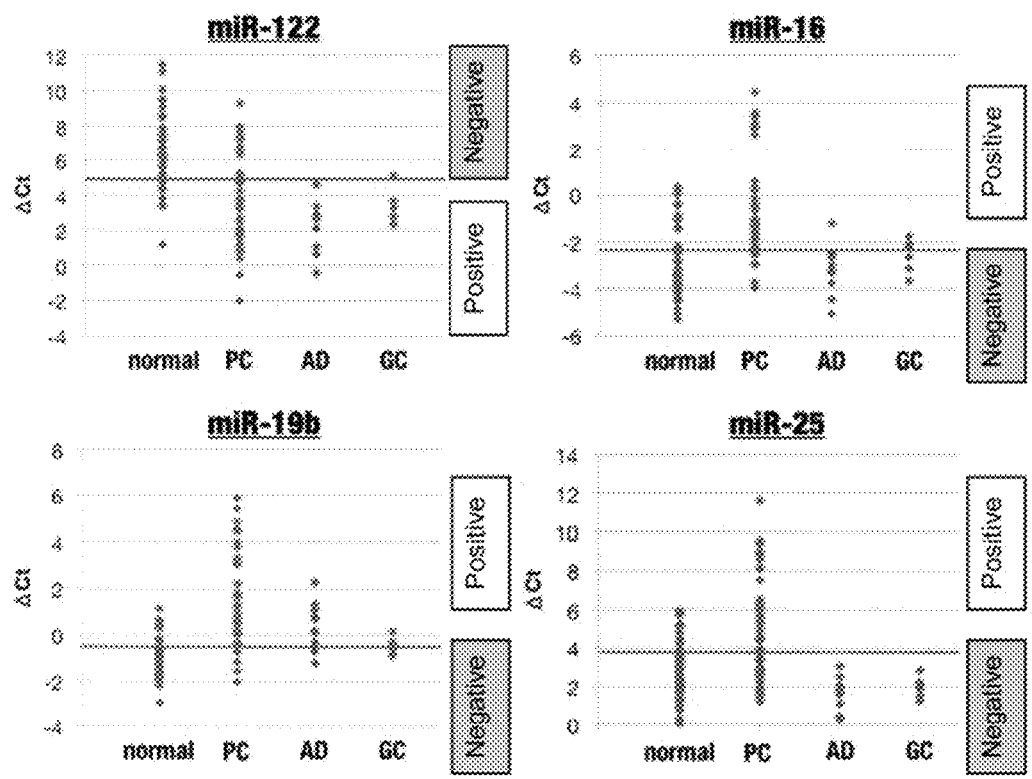
FIG. 11 shows a cut-off value and the distribution of the ΔCt value demonstrated in each sample, which were obtained in Examples below. The vertical axis represents a ΔCt value obtained by normalizing a Ct value with an external control. The blue line represents the cut-off line. normal: the healthy individuals group. PC: the pancreatic cancer patients group, AD: Alzheimer's syndrome patients group, GC: gastric cancer patients group.
Figure 12:
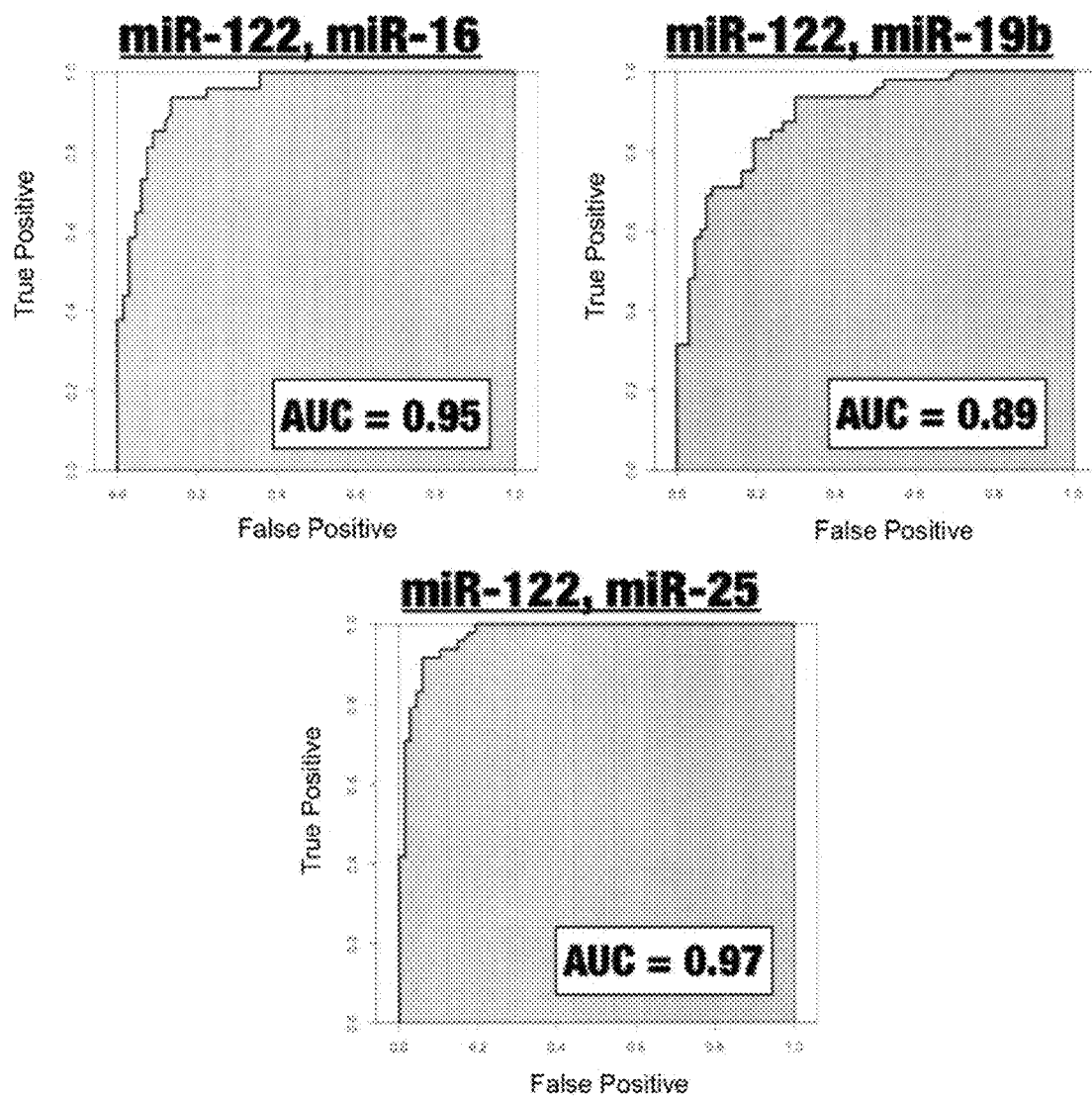
FIG. 12 shows ROC curves based on the ΔCt values of two marker miRNAs, which were obtained in Examples below.
Figure 13:
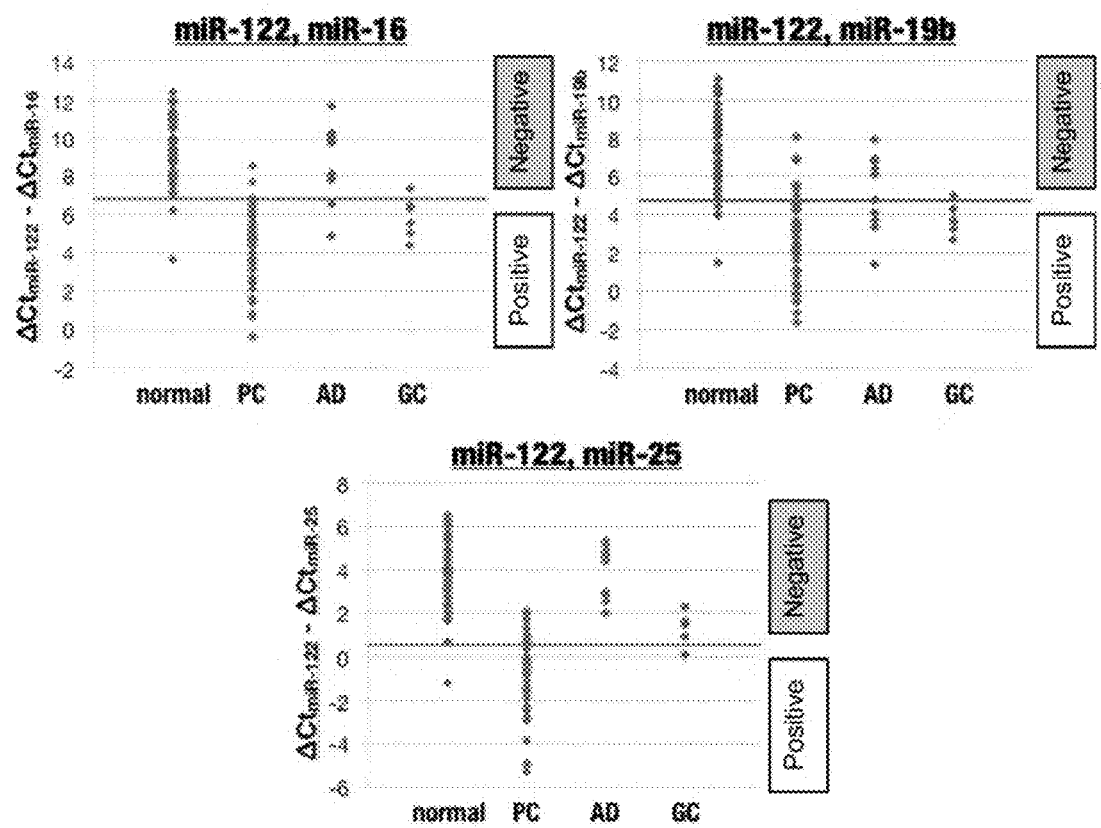
FIG. 13 shows a cut-off value and the distribution of the ΔCt value demonstrated in each sample, which were obtained in Examples below.

The created ROC curves and the AUCs are shown in FIG. 10. The grey shaded area in each graph corresponds to the AUC thereof. In general, a diagnostic marker with an AUC of $\geq 0.7$ is considered to be precise. Because all of the AUCs calculated for miR-122, miR-16, miR-19b and miR-25 were not less than 0.7, these four miRNA types are considered to be precise markers. The false positive rate and the false negative rate in the diagnosis of pancreatic cancer obtained at an optimal cut-off value in each marker miRNA are shown in Table 10, while the cut-off value and the $\Delta$Ct value of each sample are shown for comparison in FIG. 11, which cut-off value is obtained by creating a ROC curve and calculating based on the created ROC curve a cut-off value that corresponds to the minimum mean value of the false negative rate and false positive rate. FIG. 11 has indicated that a marker which has a high AUC and a low false positive rate as well as a low false negative rate is a miRNA which provides a large difference in $\Delta$Ct value between the pancreatic cancer patients group and the non-pancreatic cancer patients groups and, on the contrary, a miRNA which has a high false positive rate or a high false negative rate is a miRNA which provides a small difference in $\Delta$Ct value between the pancreatic cancer patients group and the non-pancreatic cancer patients groups, and a large overlapping portion in a collective fashion. Thus, to further enhance the difference in $\Delta$Ct value between the pancreatic cancer patients group and the non-pancreatic cancer patients groups, the difference between the $\Delta$Ct value provided by miR-122, whose miRNA amount in plasma tends to increase in the pancreatic cancer patients group, and the $\Delta$Ct value provided by either of miR-16, miR-19b and miR-25, whose miRNA amount in plasma tends to decrease in the pancreatic cancer patients group, was obtained and those combinatorial $\Delta$Ct values provided by the two miRNA types were used to create ROC curves (FIG. 12). Consequently, the obtained AUCs were shown to be not less than 0.9, which is similar to the AUC of a diagnostic marker used in clinical settings, and accordingly the combination of two miRNA types allowed a higher sensitivity to be achieved than the use of one marker miRNA type. Furthermore, it has been found that the use of two marker miRNA types increases the diagnostic accuracy relative to the diagnosis with one single marker miRNA type, because smaller values for the false negative rate and the false positive rate were demonstrated in the former case than in the latter case (Table 11). A combination of miRNAs with which the highest value of AUC was shown was the combination of miR-122 and miR-25, which was able to distinguish between pancreatic cancer patients and non-pancreatic cancer patients with very high accuracy, with AUC=0.97 and both false positive and false negative rates of 3.48% (FIG. 13).

TABLE 10

| miRNA | False positive rate (%) | False negative rate (%) | Cut-off value (ΔCt) |
|---|---|---|---|
| miR-122 | 20.9 | 9.57 | 5.31 |
| miR-16 | 13.9 | 6.09 | −2.26 |
| miR-19b | 20.0 | 6.96 | −0.455 |
| miR-25 | 8.70 | 18.3 | 3.865 |

TABLE 11

| miRNA | False positive rate (%) | False negative rate (%) | Cut-off value (ΔCt) |
|---|---|---|---|
| miR-122, miR-16 | 7.83 | 2.61 | 6.83 |
| miR-122, miR-19b | 11.3 | 6.96 | 4.72 |
| miR-122, miR-25 | 3.48 | 3.48 | 1.31 |

The invention claimed is:

1. A method for detection of miR-122-5p and miR-25-3p in a patient, said method comprising:
   detecting amounts of each of (1) miR-122-5p and (2) miR-25-3p, respectively, in a test sample separated from a living body by quantitative real-time PCR (qRT-PCR) of miRNA.

2. The method according to claim 1, wherein the qRT-PCR is performed using SYBR Green.

3. The method according to claim 1, wherein the sample is a blood sample.

4. The method according to claim 3, wherein the blood sample is plasma, serum or whole blood.

5. The method according to claim 1, further comprising determining whether an amount of miR-122-5p in the test sample is larger than a healthy control and whether an amount of miR-25-3p in the test sample is smaller than the healthy control, and wherein the larger amount of miR-122-5p and the smaller amount of miR-25-3p is statistically significant between the test sample and the healthy control.

* * * * *

SEQUENCE LISTING

<160> NUMBER OF SEQ ID NOS: 6

<210> SEQ ID NO 1
<211> LENGTH: 22
<212> TYPE: RNA
<213> ORGANISM: Homo sapiens

<400> SEQUENCE: 1
uggaguguga caaugguguu ug                                              22

<210> SEQ ID NO 2
<211> LENGTH: 22
<212> TYPE: RNA
<213> ORGANISM: Homo sapiens

<400> SEQUENCE: 2
uagcagcacg uaaauauugg cg                                              22

<210> SEQ ID NO 3
<211> LENGTH: 23
<212> TYPE: RNA
<213> ORGANISM: Homo sapiens

<400> SEQUENCE: 3
ugugcaaauc caugcaaaac uga                                             23

<210> SEQ ID NO 4
<211> LENGTH: 22
<212> TYPE: RNA
<213> ORGANISM: Homo sapiens

<400> SEQUENCE: 4
cauugcacuu gucucggucu ga                                              22

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
aaaaaaaaaa aaaaaaaaaa                                                 20

```
<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
tttttttttt ttttt                                                    15
```